United States Patent [19]
Clark et al.

[11] Patent Number: 5,643,290
[45] Date of Patent: Jul. 1, 1997

[54] PENILE CINCTURE BAND LOADING APPARATUS AND METHOD

[75] Inventors: Jeffrey W. Clark, Aiken, S.C.; Stephen J. Flynn, Peachtree City, Ga.; Steven C. Gamper, Atlanta, Ga.; Devin L. Moore, Decatur, Ga.; David S. Rowley, Smyrna, Ga.

[73] Assignee: Osbon Medical Systems, Ltd., Augusta, Ga.

[21] Appl. No.: 480,134

[22] Filed: Jun. 7, 1995

Related U.S. Application Data

[63] Continuation-in-part of Ser. No. 38,940, May 17, 1995.
[51] Int. Cl.⁶ .................................................. A61B 17/10
[52] U.S. Cl. ............................................ 606/141; 606/140
[58] Field of Search ..................................... 606/141, 140, 606/139; 128/326, 325, 327, 303, 79, 157

[56] References Cited

U.S. PATENT DOCUMENTS

| | | |
|---|---|---|
| D. 293,473 | 12/1987 | Chaney . |
| D. 317,504 | 6/1991 | Osbon . |
| D. 317,505 | 6/1991 | Osbon . |
| D. 343,454 | 1/1994 | Osbon . |
| 2,764,160 | 9/1956 | Alexander et al. . |
| 3,726,278 | 4/1973 | Scott . |
| 3,760,810 | 9/1973 | Van Hoorn . |
| 3,989,049 | 11/1976 | Yoon . |
| 4,378,008 | 3/1983 | Osbon, Sr. . |
| 4,493,319 | 1/1985 | Polk et al. . |
| 4,539,980 | 9/1985 | Chaney . |
| 4,548,201 | 10/1985 | Yoon . |
| 4,553,300 | 11/1985 | Mancha . |
| 4,628,915 | 12/1986 | Chaney . |
| 4,856,498 | 8/1989 | Osbon . |
| 4,860,746 | 8/1989 | Yoon ........................... 606/141 |
| 5,020,522 | 6/1991 | Stewart . |
| 5,083,556 | 1/1992 | Osbon et al. ................ 606/141 |
| 5,234,402 | 8/1993 | Osbon . |
| 5,244,453 | 9/1993 | Osbon et al. . |
| 5,246,015 | 9/1993 | Baber . |

*Primary Examiner*—Michael Buiz
*Assistant Examiner*—Kevin Truong
*Attorney, Agent, or Firm*—Dority & Manning Attorneys at Law, P.A.

[57] ABSTRACT

A ring loader device is used for expanding an elastic cincture band prior to application to a user's male sex organ for cincturing an engorged condition thereof as a treatment for impotence. A cone component has a conical shaped pyramid with vertical grooves. A corresponding dome component has matable ribs which are received in the cone grooves. The ribs enter the grooves and align the cone and dome as they are matably pressed together. As a prior step, a suitable elastic ring is placed over the tapered smaller end of the cone component, and becomes expanded against the cone outer surface as the dome is pressed onto the cone. The cone may include particular surface contours for corresponding receipt of inside diameter features of the elastic ring, such as a urethra channel or radially inward points for added cincturing pressure. The cone and dome arrangement may be used to expand and align an elastic ring onto a transfer collar, or directly onto the outside diameter of a vacuum chamber. Lubricant applied to the exterior of the cone is beneficially swept by a thrust with the dome mechanism during ring expansion onto the ring and onto a receiving transfer collar or vacuum chamber. The presence of the lubricant after expansion permits the elastic ring to be rotated as desired. Visual elements assist desired alignment of elastic ring inside diameter features, which are otherwise difficult to discern after the elastic ring is expanded onto a further element.

34 Claims, 8 Drawing Sheets

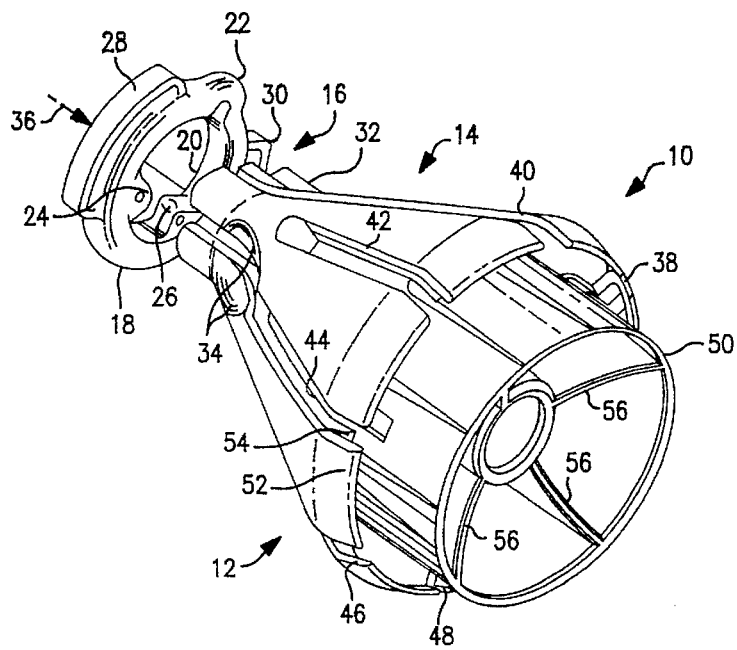
FIG. 1
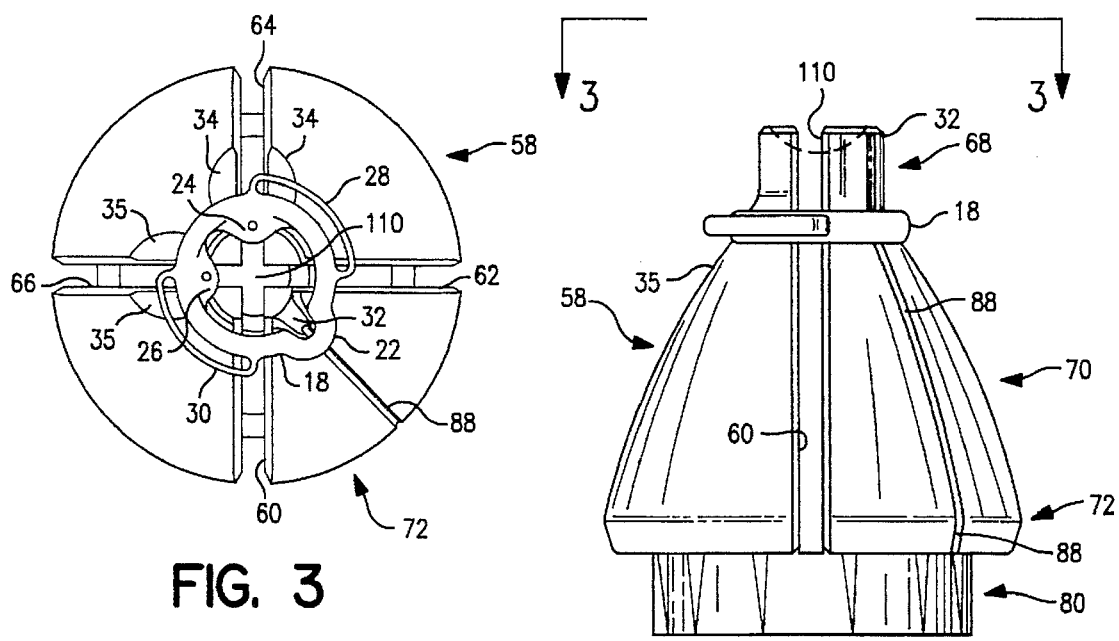
FIG. 3
FIG. 2

PENILE CINCTURE BAND LOADING APPARATUS AND METHOD

This is a continuation-in-part application of application Ser. No. 29/038,940, filed May 17, 1995, with the present inventors for "ELASTIC CINCTURE BAND EXPANSION DEVICE FOR THE TREATMENT OF IMPOTENCE."

BACKGROUND OF THE INVENTION

The present application concerns apparatus for resilient penile cincture band operations in general, and more particularly, a device for expansion and transfer of a resilient penile cincture band and methods thereof.

The problem of male impotence (i.e., the inability to gain an adequate penile erection for coitus) is well known and the subject of a considerable scientific and medical activity. Various surgical and nonsurgical therapies are available for treatment of male impotence. One therapy makes use of a vacuum chamber device for producing penile engorgement and rigidity by drawing blood into the erectile bodies of the user's male sex organ, i.e., the penis. The subject's penis is placed within a vacuum chamber or cylinder for producing engorgement which condition may typically be subsequently secured with an elastic cincture band or the like.

U.S. Pat. Nos. 4,378,008 (Osbon, Sr.) and 4,856,498 (Osbon) disclose examples of vacuum chambers for use in conducting vacuum erection enhancement therapy. Also illustrated are examples of elastic bands or cincture rings for securing an engorged condition. The disclosures of both such patents are hereby incorporated herein by reference. In general, such cincture bands are enlarged and placed as shown about the distal or open entrance end of the vacuum chamber so as to be readily advanced onto the base of the user's male sex organ after its engorgement. Both such patents, as well as U.S. Pat. No. 293,473 (Chaney) and U.S. Pat. No. 4,539,980 (Chaney) disclose examples of resilient penile cincture bands, both with and without handles.

One of the known somewhat problematic aspects of utilizing vacuum erection enhancement therapy concerns the simple necessity of handling the apparatus itself. Because of the relatively small size of the resilient penile cincture band, the relatively high resiliency thereof, and the acts involved in its use, some degree of user strength and dexterity is involved with its placement and with practice of the overall therapy. Of course, the degree of "difficulty" encountered by each user at a given time tremendously varies subject to numerous highly subjective factors and considerations. Such is equally true whenever a cincture band is utilized for securing an engorged penile condition, regardless of whether vacuum therapy is used to induce such condition, or if other methods or techniques are used.

U.S. Pat. Nos. 4,539,980 and 4,628,915 (Chaney) disclose an accessory generally for use in expanding an elastic ring for contracting on the penis to maintain an erection. As illustrated for example in FIG. 5 of the '980 patent and FIG. 2 of the '915 patent, a cone portion is integrally formed with a cylindrical portion which removably receives a sleeve thereover. The sleeve is secured by fitting of a tapered pin, for example such as a spring-loaded spindle or the like, which is associated with an exposed portion of the cylindrical region after passage of the sleeve thereover. The small end of the cone is closed and a number of separate parts are required for temporarily securing the removable sleeve along the length of the cylindrical portion and relative the cone for receiving an expanded elastic ring therefrom.

U.S. Pat. No. 5,083,556 to Osbon, et al. discloses a cone-shaped expansion member against which a cincture band may be expanded and then transferred onto a vacuum chamber or transfer collar.

The disclosures of all the above patents are fully incorporated herein by reference.

SUMMARY OF THE INVENTION

The present invention recognizes and addresses various of the foregoing problems, and others, concerning elastic penile cincture band operations. Thus, broadly speaking, a present main object is improved penile elastic cincture band operations. More particularly, a present main concern is improved cincture band handling operations, such as expansion of an elastic band and/or subsequent transference thereof to another structure such as either a vacuum chamber erection device or an intermediate transfer collar.

It is another more particular object of the present invention to provide improved apparatus and method for expanding an elastic penile cincture band, including improved construction and subsequent maintenance (i.e., cleansing and the like) thereof.

It is yet another more particular present object to provide such an improved apparatus which further facilitates subsequent transference of the expanded band directly onto the outside diameter of a vacuum generating penile erection chamber or to the outside diameter of a transfer collar for subsequent application to the base of a user's male sex organ.

Still a further present broad object is to provide improved apparatus for expansion and/or other handling of a resilient cincture band, for ease of the patient's use, thereby improving efficiency of and confidence in the associated impotence therapy.

It is another more particular object to provide such improved apparatus usable with either vacuum erection enhancement therapy, or usable with other engorgement producing techniques for subsequent securement of an engorged condition with a resilient penile cincture band.

Another object is to provide apparatus and method making use of cone and dome components to obtain a mechanically-aided expansion of a tension ring for impotence treatment. More particularly, apparatus and method are provided for the use of mated cone grooves and dome ribs to establish alignment (i.e., keying) and a working stroke between the cone and dome.

Still further with respect to the cone surface, contours preferably may be provided thereon for proper and identifiable ring alignment, such as relative to the presence of a urethra channel or pressure point-type features of the ring itself.

Still further, it is one present object to provide at least a slight interference fit so as to desirably hold the cone and dome features together at the end of the expansion stroke. In connection therewith, it is the present object to provide a disconnect button in the top of the dome for ease of separating the mated cone and dome components, which button assembly preferably is also removable for ease of cleaning the dome interior.

It is a still further present object to provide an advantageous methodology concerning the practice of lubricant, wherein the surface sweeping action of the expansion stroke results in an expanded ring which is also lubricated for ease of adjustment and transfer from a collar and/or vacuum cylinder.

Additional objects and advantages of the invention are set forth, or will be apparent to those of ordinary skill in the art, from the detailed description which follows. Also, it should be appreciated that modifications and various to the specifically illustrated and discussed features hereof may be practiced in various embodiments and uses of this invention without departing from the spirit and scope thereof, by virtue of present reference thereto. Such variations may include, but are not limited to, substitution of equivalent means and features (or materials) for those shown or discussed, and the functional or positional reversal of various parts or features, or the like.

Still further, it is to be understood that different embodiments, as well as different presently preferred embodiments, of this invention may include various combinations or configurations of presently disclosed features, steps, or elements, or their equivalents (including combinations of features or steps or configurations thereof not expressly shown in the Figures or stated in the detailed description).

One exemplary such embodiment of the present invention relates to an improved impotence treatment system for augmenting male potency through vacuum-generated engorgement of the male sex organ and subsequent cincture thereof with a cincture band. Such a system preferably comprises an elongated, generally cylindrical vacuum chamber, an elastic penile cincture band, and particular cincture band expansion means, having in combination both expanding cone means and corresponding actuation means.

Such vacuum chamber is preferably adapted to cover a male sex organ, and is open at a proximal longitudinal end thereof for contact with a user and for passage of the user's male sex organ therethrough into the chamber interior. Such cincture band is adapted to be expanded and located about the vacuum chamber proximal end for subsequent movement onto the base of a user's male sex organ for cincturing an engorged condition thereof.

The above-referenced cincture band expansion means is preferably removably associated with the vacuum chamber proximal end for expanding the cincture band and for locating same onto the vacuum chamber whenever the expansion means are associated therewith. The expanding cone means of such expansion means are preferably provided for receiving thereon a cincture band to be expanded. The corresponding actuation means are matable with the cone means for being pushed by a user down onto the cone means such that a cincture band received on the cone means is thereby expanded for subsequent cincturing of a user's engorged male sex organ.

The foregoing system may be further provided with alignment means as part of the cincture band expansion means, for aiding alignment and mating of the cone means and the actuation means. Such an arrangement may include at least one slot and corresponding matable ribbed element formed with the cone means and actuation means, respectively.

In other embodiments, the cincture band inside diameter may include a particular feature, such as a urethra channel, and the expanding cone means may be provided with a corresponding surface contour element adapted for matable receipt of such cincture band inside diameter feature.

Additional features may further alternatively be practiced in combination with the above improved impotence treatment system, all in accordance with the subject invention, and as further described herein.

Another present exemplary embodiment concerns more particularly a ring loading device, such as for use with an elastic ring of the type for augmenting male potency by cincturing an engorged condition thereof. Such device may comprise, in combination, a particular expansion cone and corresponding actuation dome.

Such an expansion cone may have a generally circular, enlarged base and a tapered outside surface reducing to a relatively smaller diameter end. Such smaller end may be adapted for receipt thereabout of an elastic ring which is to be enlarged.

In turn, the actuation dome may be adapted to be received downwardly about the tapered smaller end of the expansion cone and forced therealong. Such movement engages an elastic ring received on the expansion cone for expansion of such ring towards the base of the cone. Alternatively, such expansion cone may include at least one vertical groove therealong, with the actuation dome provided with at least one rib adapted to be received in such vertical groove for alignment of the cone and dome during relative movement therebetween. A plurality of cone grooves and corresponding dome ribs may be practiced. Additional alternative features may be included in particular embodiments.

Those of ordinary skill in the art will appreciate that the subject invention fully encompasses corresponding methodology, as suggested and apparent from the present disclosure throughout. One such exemplary methodology relates to an improved impotence treatment method for augmenting male potency through vacuum-generated engorgement of the male sex organ and subsequent cincture thereof with a cincture band. Such methodology is usable with a system such as comprising an elongated, generally cylindrical vacuum chamber adapted to cover a male sex organ, with an open proximal longitudinal end thereof contacting the user and receiving the user's male sex organ therethrough, as generally referenced above. The methodology would in such instance involve further using an elastic penile cincture band adapted to be expanded and located about such vacuum chamber proximal end for subsequent movement onto the base of a user's male sex organ for cincturing an engorged condition thereof, as well understood by those of ordinary skill in the art.

The present improved method operative with such a system may include various steps, such as providing a cone component comprising a generally conical-shaped pyramid adapted to be removably associated with the vacuum chamber proximal end. Such a cone component is provided for expanding the cincture band and for locating such cincture band onto the vacuum chamber outside diameter whenever the cone component is associated therewith.

Still further, in accordance with such methodology, a dome component is provided matable with the cone component and adapted to be pushed down by a user onto the cone component, with a cincture band received on the cone component.

In accordance with the methodology, a cincture band is placed onto the relatively smaller end of the cone component, and the dome component is then placed down onto the cone component with the cincture band seated thereon. The dome component is pressed downward towards the cone component for expansion of the cincture band. Additional features and steps may be practiced in various embodiments of such, and other, present methodology.

Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures, in which:

FIG. 1 is a generally side and bottom perspective view of a first embodiment of a cone component in accordance with the present invention, having eight slots or grooves, and represented in conjunction with a specialized elastic penile cincture band of one type preferably usable therewith;

FIG. 2 is a generally side elevational view of a second exemplary embodiment of a cone component in accordance with the subject invention, having four slots or grooves, and illustrated with a specialized elastic cincture band (as in FIG. 1) received thereon, prepared for expansion;

FIG. 3 is a generally end elevational view of the exemplary cone component of present FIG. 2, illustrated along the view line 3—3 shown therein;

Figure 4:
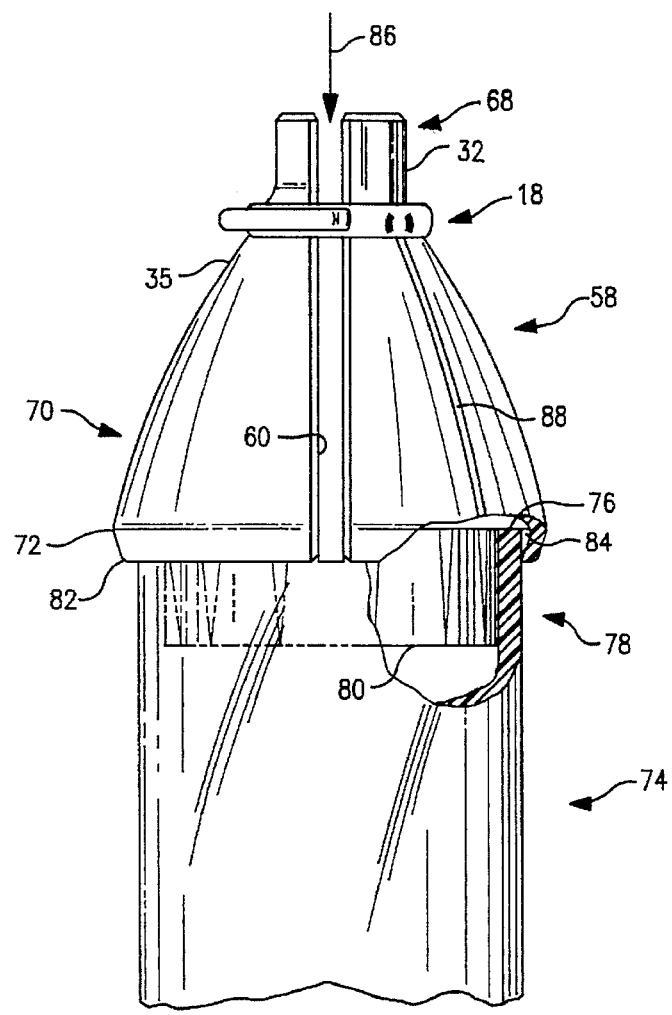
FIG. 4 is a generally side elevational view of the exemplary cone embodiment of present FIG. 2, with the exemplary specialized elastic ring seated thereon, and with such arrangement seated in turn on a pertinent illustrated portion of an exemplary vacuum chamber, with such view being shown in partial cutaway to illustrate the mounting relationship between the cone and vacuum chamber.

Repeat use of reference characters throughout the present specification and appended drawings is intended to represent same or analogous features or elements of the invention.

DETAILED DESCRIPTION OF THE PREFERRED EMBODIMENTS

While various embodiments may be practiced in accordance with the subject invention, the following exemplary embodiments are representative of certain presently preferred features, and represent certain preferred methodologies, as indicated. FIG. 1 illustrates a first embodiment of a cone component or expanding cone means 10. Such expansion cone (and its corresponding actuation component) may form part of a ring loading device or be combined as part of a larger improved impotence treatment system in accordance with the present invention.

Expansion cone 10 has a generally circular, enlarged base, generally 12, and a tapered outside surface 14 reducing to a relatively smaller diameter end 16 thereof. As FIG. 1 represents, such smaller end 16 is adapted to receive an elastic ring which is to be enlarged with use of cone means 10.

FIG. 1 illustrates an exemplary elastic ring or elastic penile cincture band 18, which may be used. A more detailed example of such elastic ring 18 is set forth in U.S. Design Pat. No. D343,455 and U.S. Pat. No. 5,306,227, the disclosures of which are fully incorporated herein by reference. As shown, such ring has a generally circular inside diameter 20 with several additional noncircular features which may be practiced. Such features may include a urethra channel 22 for alignment with a user's urethra, for greater comfort and function during use of elastic ring 18. Also, radially inwardly projecting points 24 and 26 may be provided for supplying additional pressure to specific strategic locations on the user's male sex organ, for improved cincturing thereof. Handles, such as 28 and 30, may also be practiced.

While an elastic ring such as 18 having additional inside diameter features provides certain advantages, it also presents particular problems if it is to be expanded mechanically. To address such difficulties, the present invention provides outer surface slope 14 with corresponding surface contours for matable receipt with any such corresponding features formed in the inside diameter of the elastic ring. For example, an elongated projection 32 formed along at least a portion of the expansion cone outer surface 14 serves to make matable contact with the elastic ring urethra channel 22.

Not only does such arrangement facilitate expansion of the elastic ring, but it also helps rotatably align ring 18 in a known, desired position. Such fact is extremely beneficial in that inside diameter features of an expanded elastic ring may be virtually impossible to detect, due to the flattening out effect which can occur when such ring is placed under tension. While relative rotation of the elastic ring around the base of the user's penis may be possible, the necessity of such is to be avoided in light of the further possibility of entrapped pubic hairs, skin, or other factors which limit the desirability of having to rotate the ring after it is so positioned.

Also, in the case of the additional points 24 and 26, it is desired that such pressure be applied as quickly as possible upon application of the elastic ring, in order to gain full benefit thereof. Having to rotatably adjust the elastic ring once applied to the base of the user's penis is, therefore, one major drawback which can be totally avoided through practice of the present invention.

Outer surface 14 may be further provided with surface contours, such as depressions 34, located for receiving radially inward point 24. It will be understood that additional such depressions may be formed on a corresponding portion of surface 14 for accommodating radially inward point 26.

It will be further appreciated that surface contours such as 32 and 34 may be varied in accordance with the present invention and different embodiments thereof, to accommodate other forms of elastic rings having other (or having even no) inside diameter features. Examples of other rings which may be practiced in accordance with this invention are illustrated in U.S. Pat. Nos. 4,378,008; 4,856,498; U.S. Design Pat. No. D317,504; U.S. Design Pat. No. D317,505; U.S. Pat. Nos. 5,083,556; 5,234,402; 5,244,453; and U.S. Design Pat. No. D343,454; the disclosures of which patents are all incorporated herein by reference.

It is to be understood from the generally side and bottom perspective view of cone 10 (FIG. 1) that elastic ring 18 is placed over tapered smaller end 16 thereof, and further advanced in the direction of arrow 36 against the outer cone surface 14 so as to be enlarged thereby. To facilitate such movement, an actuation dome or similar features in accordance with the subject invention (further discussed below) is provided so as to collectively comprise the subject ring loading device, and to serve as elements of the present improved impotence treatment system.

Such relative or mated movement of the dome component or actuation means and the cone component are preferably aligned and facilitated through the use of at least one groove or slot formed in the cone component, to which a rib or similar element of the dome component is mated. The exemplary embodiment of cone 10 as shown in FIG. 1 includes eight such slots formed with cone means 10 and extending vertically (i.e., longitudinally) therealong. Such slots or grooves 38, 40, 42, 44, 46, 48, and two others not seen in the illustration of present FIG. 1, may be placed equidistantly about the circumference of cone 10.

As shown, certain of the grooves or slots (such as 40 and 44) extend further along through the longitudinal length of cone 10, and penetrate tapered smaller end 16 thereof. As discussed below, such arrangement permits early alignment and mating of the dome component with the cone component. Other slots, such as 38, 42, and 46, are subsequently engaged as the dome component further mates with the cone component.

Cone means 10 includes a relatively reduced diameter base 50 for engaging a further element to which an expanded elastic ring is to be applied, such as either a transfer collar or the outside diameter of a vacuum chamber. In general, a circumferential portion 52 of expansion base 12 overhangs an annular stop element 54 adjacent reduced base 50. Such reduced base 50 may also be slightly tapered to facilitate its insertion into the further receiving element, until such element is seated against annular stop element 54.

Such reduced diameter base 50 may also be provided with internal elements, such as members 56, for the purpose of grasping and handling the cone component after the dome is applied thereto. Such finger grasps not only assist in separation of a mated cone and dome pair, but also provide a holding surface for cone 10 other than the outside surface 14 thereof, which may during the course of use become coated with a thin layer of personal lubricant.

FIGS. 2 and 3 respectively illustrate side and end elevational views of a second exemplary embodiment of a cone component 58 in accordance with the subject invention, having four slots or grooves therein, instead of the eight illustrated in present FIG. 1. As represented, the grooves 60, 62, 64, and 66 are preferably spaced equidistance about the circumference of cone 58, for maximized strength and alignment stability. As shown in FIG. 2, at least in the vicinity of tapered end 68 and along the generally conical-shaped pyramid outer surface or slope 70, the grooves penetrate through the cone to permit corresponding ribs to likewise penetrate the cone and completely drive elastic ring 18 from its initial position shown in FIGS. 2 and 3, past the enlarged base 72.

As discussed above, a surface contour 32 may be provided to accommodate urethra channel 22, while surface depressions or indentations 34 and 35 may be provided to accommodate respective points 24 and 26. Other external cone surface contours may be practiced, as referenced above.

FIG. 4 is a generally side elevational view of the exemplary cone embodiment 58 of present FIGS. 2 and 3, with the exemplary specialized elastic ring 18 seated thereon. When further propelled in the direction of enlarged base 72, the elastic ring 18 is expanded for subsequent use. Those of ordinary skill in the art will appreciate that various personal lubricants may be applied to outer surface 70 to facilitate such expansion step.

FIG. 4 further represents, in partial cutaway, an exemplary generally cylindrical vacuum chamber 74 which may be practiced with the present invention or form part of a treatment system in accordance with the subject invention. Since vacuum chambers are generally well known, a lower portion of such vacuum chamber (and other features, such as a vacuum tube and connected hand pump) are not shown, for the sake of simplicity. Vacuum chamber 24 and the discussion thereof as set forth in U.S. Pat. No. 5,083,556, is one known example, and all of such disclosure is fully incorporated herein by reference.

Vacuum chamber 74 has an open proximal end 76 into which a user's male sex organ may be placed for subsequent vacuum-generated engorgement thereof. Prior to such time, an elastic ring or cincture band may be expanded onto the vacuum chamber outside diameter generally 78 adjacent such open end, after which the elastic ring may be slipped onto the base of the engorged penis, for cincturing such engorged condition, as is well understood by those of ordinary skill in the art.

The subject invention, in part, may comprise cincture band expansion means removably associated with such vacuum chamber proximal end 76 for expanding a cincture band 18 or the like and for locating such onto the vacuum chamber (in the vicinity of outside diameter 78) whenever the expansion means are associated with such vacuum chamber. FIG. 4 illustrates such condition, wherein the reduced diameter base 80 of cone 58 is placed into the open proximal end 76 of vacuum chamber 74. A circumferential overhang portion 82 extends beyond end 76. End 76 abuts a circumferential stop 84 formed beneath overhang 82. In such fashion, elastic ring 18 may be expanded in the direction of arrow 86 until it passes over the expanded base 72, past the overhang 82 and onto the outside diameter 78 of vacuum chamber 74. The expanded elastic ring 18 is then ready for application to a user's penis in accordance with vacuum-generated engorgement therapy.

Advantageously and in accordance with the subject invention, by applying a very thin layer of personal lubricant fairly evenly about cone surface 70, the expansion effort for elastic ring 18 is facilitated and a surface sweeping action as the ring is expanded causes a layer of such lubricant to be deposited between the expanded ring and the outside diameter 78 of vacuum chamber 74. Such result is a significant benefit, as noted above, with respect to ease of any adjustment of expanded ring 18 before it is placed around the base of a user's penis.

As referenced above, one beneficial aspect of the subject invention involves both establishing and identifying the rotational ring alignment or registration, since such is otherwise difficult to discern once the ring is expanded onto the vacuum chamber. In addition to the extended element 32 and depressions 34 and 35 noted above, a visual guide element 88 may be provided extending along the expansion cone to the base thereof, for indicating the position of a certain portion of the elastic ring, such as the urethra channel thereof. Such feature, particularly combined with the resulting lubrication described above, permits the enlarged ring to be readily adjusted as needed before being applied to the base of the user's penis.

As an alternative to use with a vacuum chamber 74, cone component 58 (or cone component 10) may be directly engaged with a transfer collar. One example of such a transfer collar is shown by element 44 in FIG. 4 of U.S. Pat. No. 5,083,556, the complete disclosure and related discussion of which is fully incorporated herein by reference. As understood by those of ordinary skill in the art, an expanded elastic ring may be carried on such a transfer collar and subsequently used by direct application to the base of the penis (with the penis passed through the longitudinal channel of such transfer collar), or with the enlarged ring transferred onto a vacuum chamber about the outside diameter thereof, for use generally as discussed above in conjunction with the illustration of present FIG. 4. All such alternative arrangements for receiving a ring from a ring loading device in accordance with the subject invention, are intended to come within the spirit and scope of the subject invention by present reference thereto.

Figure 5A:
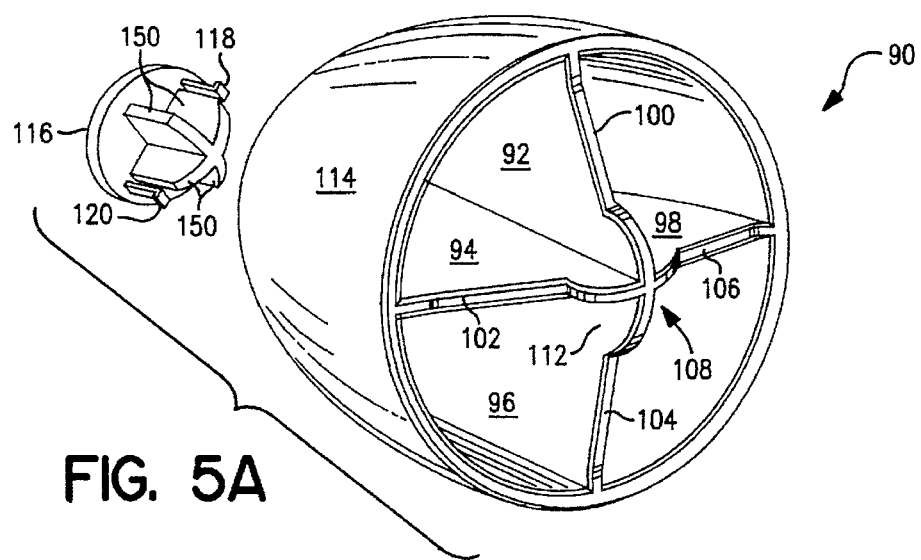
FIG. 5A shows a generally side and bottom perspective view of a dome component embodiment in accordance with the subject invention, having four ribs for operative and functional mating with the exemplary four slot cone of present FIGS. 2 through 4, and with a removable release button shown in exploded view relative thereto.

FIGS. 5A, 5B, 6, 7, and 8 illustrate various views of an exemplary alignment means or expansion cone generally 90 in accordance with the subject invention, and particularly adapted for use with the four slot exemplary cone 58. FIG. 5A illustrates a generally side and bottom perspective view of dome component 90, having four ribs 92, 94, 96, and 98 for operative and functional mating with the exemplary four slots 60, 62, 64, and 66 of cone 58. Each rib is connected within the interior of the otherwise cap or hat shaped device 90. The matrix of such ribs as illustrated provides effective strength of the dome while also initiating and maintaining alignment of the dome 90 and cone 58 during use.

More specifically, each respective rib has an angled lower surface or leading edge 100, 102, 104, and 106 which engages and propels the elastic ring otherwise received on the cone outer surface, as the dome and cone are mated. The edges of such four ribs 92, 94, 96, and 98 may intersect to form an "X" key generally 108, which may be mated with a corresponding "X" keyhole 110 (FIGS. 2 and 3) generally formed in the end 68 of cone 58. As represented in FIG. 5A, the dome ribs include an extended region generally 112 in the vicinity of "X" key 108, for facilitating initial engagement of the ribs with their corresponding grooves.

Figure 5B:
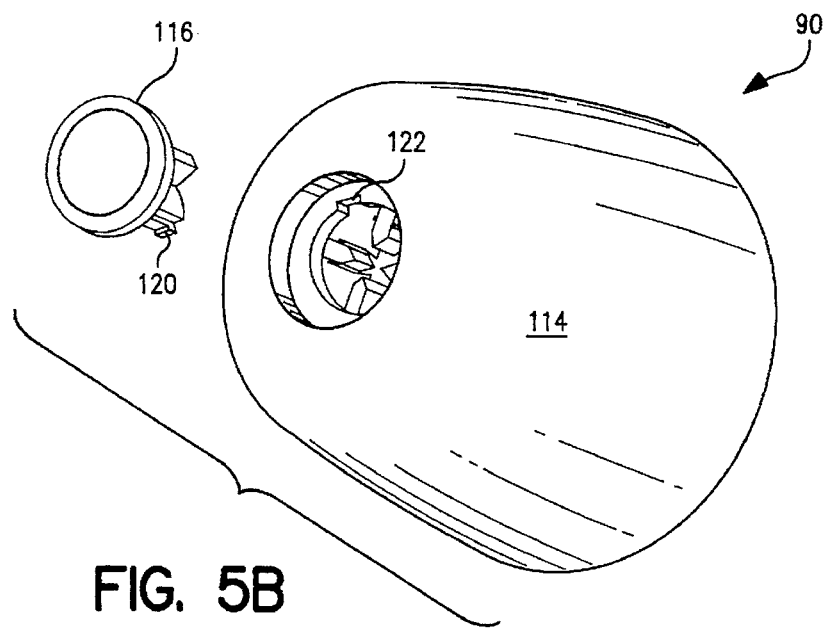
FIG. 5B is a generally side and top perspective view of the exemplary four rib dome component of present FIG. 5A, with the removable release button again shown in exploded view relative thereto.

FIG. 5B is a generally side and top perspective view of the exemplary four rib dome component 90 of the present invention as discussed in conjunction with FIG. 5A. The exterior surface generally 114 is relatively smooth and unadorned, with the exception of a removable release button generally 116 shown in exploded view in both FIGS. 5A and 5B. As will be discussed in greater detail below, release button 116 (comprising part of interference release means) has a pair of opposing catches 118 and 120, which may engage corresponding openings 122 and 124 (not shown in FIG. 5B), for selective retention of button 116. Such removability permits the interior of dome component 90 to be periodically thoroughly washed, which promotes hygiene. This may be a particular need in view of the fact that personal lubricant typically present throughout use, may tend to have build up on the dome interior, and would otherwise be possibly difficult to remove.

As discussed in greater detail below, the purpose of such release button is to push against tapered end 68 whenever it is desired to separate mated cone and dome components 58 and 90, to break a preferred slight interference fit therebetween, as discussed in greater detail below.

Figure 8:
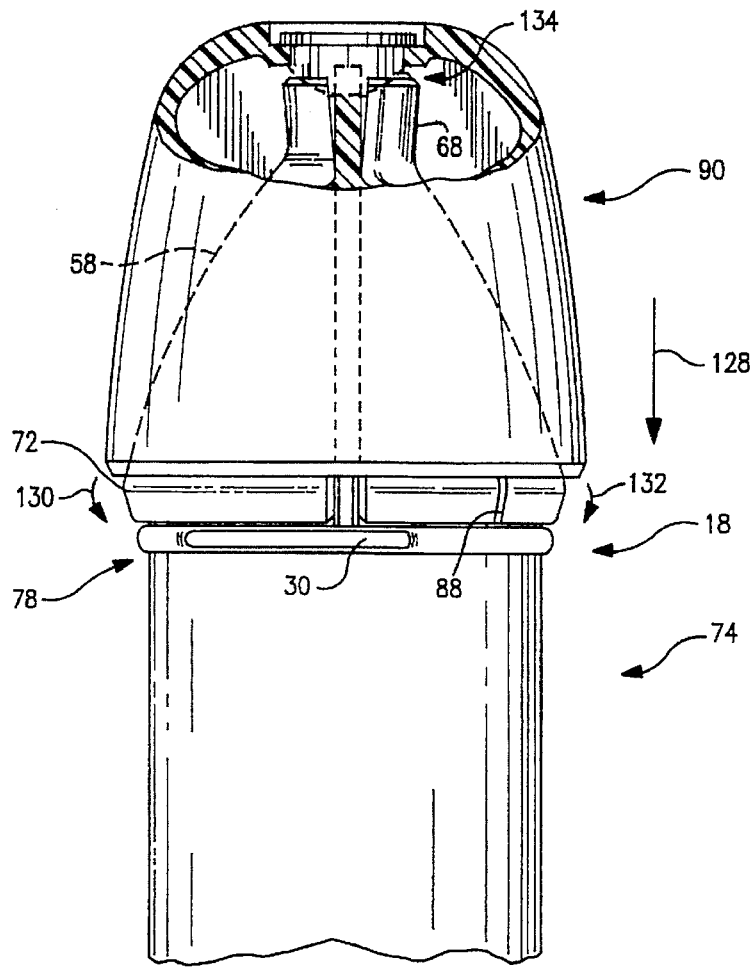
FIG. 8 is a further side elevational view of the subject matter of FIGS. 6 and 7, illustrating a completed expansion function, with the exemplary dome component completely received over the corresponding mated exemplary cone component, and with the exemplary specialized elastic ring fully expanded and transferred onto the end of the representative vacuum chamber, and further with the cone and dome components in temporary interference fit, as represented within the partial cutaway illustration of the dome component.
Figure 6:
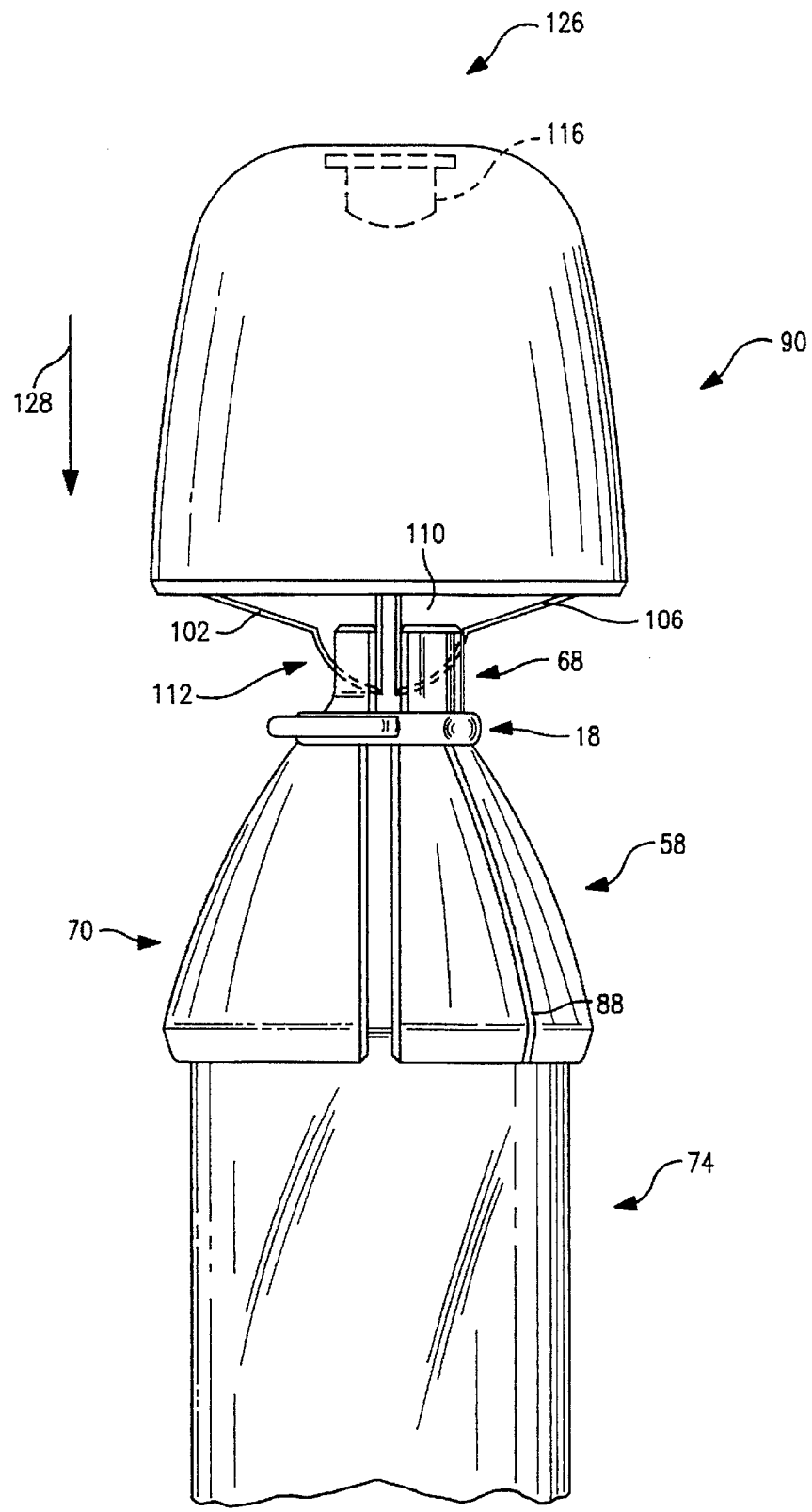
FIG. 6 is a generally side elevational view illustrating in combination the exemplary four slot cone component and vacuum chamber mounting arrangement of present FIG. 4, further with an exemplary specialized ring mounted thereon for expansion, and with the exemplary four rib dome component of present FIG. 5A keyed to the cone component for the expansion function, but prior to application of any expansion force.
Figure 7:
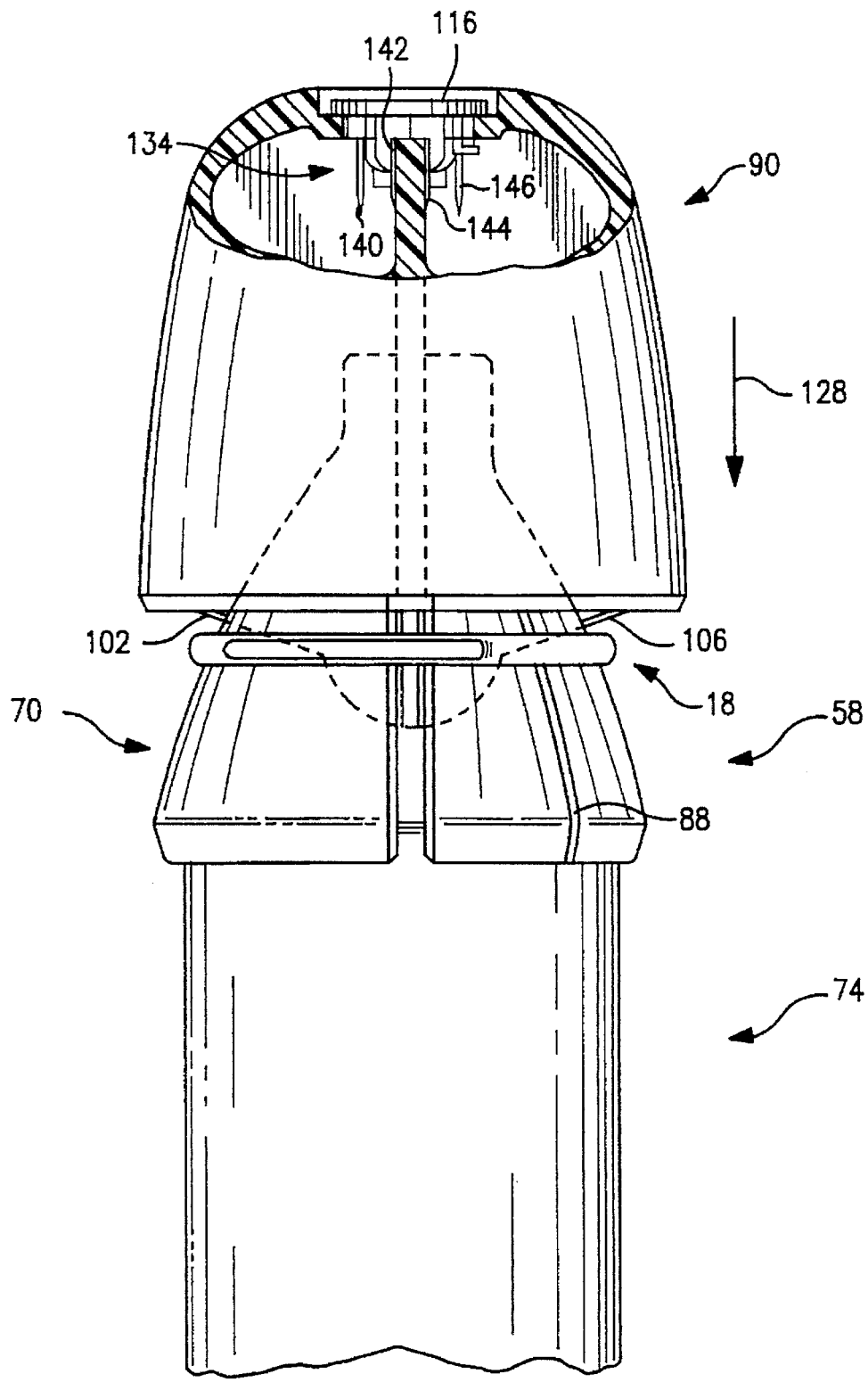
FIG. 7 is a generally side elevational view of the components of present FIG. 6, with such expansion function in progression, such that the exemplary specialized elastic ring is illustrated as being approximately half-way expanded, moved about one-half along the sloping external surface of the exemplary cone component, and illustrating the dome component in partial cutaway.

FIGS. 6, 7, and 8 represent a progression of side elevational views of components in combination, including the exemplary four slot cone component 58 and vacuum chamber 74 mounting arrangement as shown in present FIG. 4, further with the exemplary specialized ring 18 mounted thereon for expansion, and with the exemplary four rib dome component 90 of present FIG. 5A keyed to the cone component 58.

As represented in present FIG. 6, ring 18 has been initially placed (but not expanded) over tapered smaller end 68 of cone 58. The extended key region generally 112 of dome 90 has been threaded or placed into the corresponding "X" keyhole generally 110 of cone 58. With such an arrangement, a user may press with a quick thrust or other action on end 126 of dome 90 to drive both the dome and elastic ring 18 in the direction of arrow 128, which is generally aligned along the longitudinal axis of vacuum chamber 74.

As shown, exemplary leading edges 102 and 106 of dome ribs are situated at a predetermined angle relative to a plane perpendicular to direction line 128. Such predetermined angle is preferably in a range of from about 15 degrees to about 45 degrees, so as to effectively force elastic ring 18 along cone surface 70 as dome 90 is advanced in the direction of arrow 128.

FIG. 7 illustrates partial depression or mating of dome 90 onto cone 58 in the direction of arrow 128. Elastic ring 18 has been expanded about half-way and is otherwise moved about half-way along cone surface 70. As represented, it is already somewhat difficult to discern where particular inside diameter features of elastic ring 18 may be located. Hence, the locator strip 88 or similar feature used along the outside of cone 58, represents the location of a predetermined feature, such as the urethra channel (whenever the elastic ring is initially correctly placed over tapered smaller end 68, as discussed above).

As represented, leading rib edges 102 and 106 are in engagement with ring 18 and serve to convey the driving force thereto from dome 90. At the same time, it is to be understood by those of ordinary skill in the art that the ribs associated with leading edges 102 and 106 (as well as any other number of ribs which may be present, such as two additional ribs in the case of dome embodiment 90), are penetrating cone 58 by passing into their corresponding mated slots or grooves. Hence, the dome and cone continue to be aligned for stable mating, all of which results in a significantly mechanically advantaged cincture band expansion means arrangement (i.e., the operative combination of the expanding cone means 58 and the actuation means 90).

FIG. 8 shows a further side elevational view of the structures of FIGS. 6 and 7, essentially after a completed expansion or mating step. As a result, elastic ring 18 has been fully expanded and placed onto the outside diameter 78 of vacuum chamber 74, having passed over the fully expanded base 72 (see arrows 130 and 132). In such instance, as shown by partial cutaways in both FIGS. 7 and 8, a particular interior section generally 134 of dome 90 has received tapered smaller end 68 of cone 58, and formed an interference fit therewith. The mechanics of such interference fit are discussed in greater detail below with reference to enlarged partial sectional views of FIGS. 9 and 10.

Figure 11:
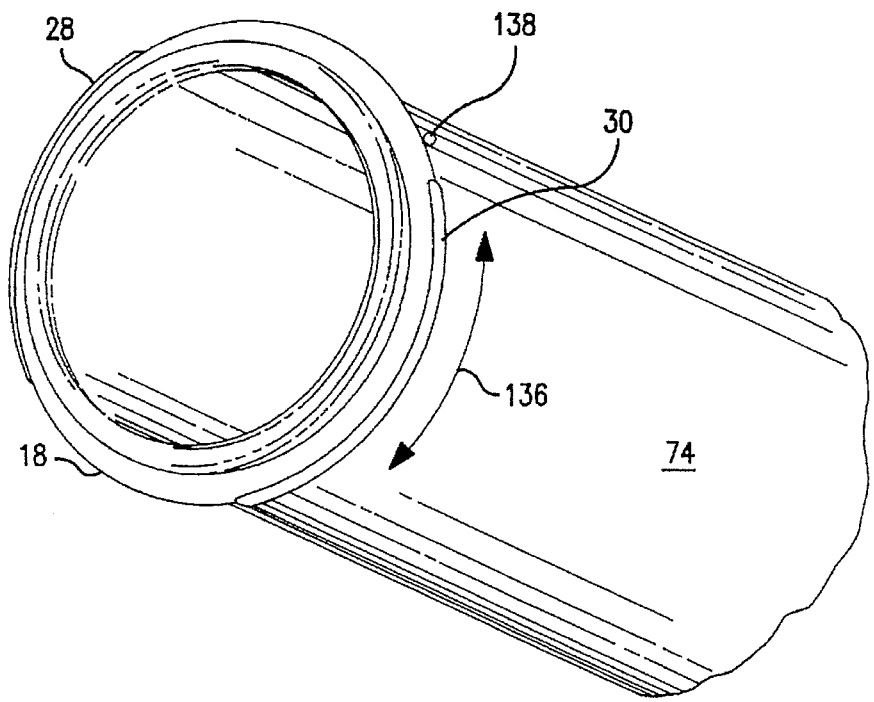
FIG. 11 is a generally side and end perspective view of an exemplary vacuum chamber with the exemplary specialized elastic ring expanded and received thereon, such as through practice of the present invention prior to application of vacuum therapy to a patient.

FIG. 11 represents the resulting placement of enlarged elastic ring 18 onto the outside diameter of vacuum chamber 74. As illustrated, any reference to any inside diameter features of ring 18 is difficult to discern, after its enlargement. However, by noting the position of visual indicator element 88 (FIG. 8) prior to separation of the dome and cone from vacuum chamber 74, the user may be informed as to where a particular feature, such as the urethra channel, is located. Since such inside diameter feature corresponds with a unique portion of the human anatomy, the complete cincture band is properly registered by alignment of one such feature.

To make use of such registration feature prior to application of the expanded ring to the user's penis, it may be desired (or necessary) to rotatably adjust the position of elastic ring 18, such as in the relative direction of two-headed arrow 136 (FIG. 11). To improve use of the registration information, a visual indication of alignment may also be placed on vacuum chamber 74, such as a slight extension or a recess 138. Thereafter, appropriate alignment can be made between visual indicator element 88 on the cone and 138 or similar on the vacuum chamber.

In the present exemplary illustrations, it is otherwise known from the design of the elastic ring that the urethra channel 22 thereof is located approximately half-way between adjacent ends of handles 28 and 30. In both FIGS. 8 and 11, it is apparent that the visual alignment elements 88 and 138 are not situated approximately half-way between the closer pair of ends of ring handles 28 and 30. However, due to the lubrication application advantages of the subject invention as referenced above, ring 18 may be readily positioned as needed by rotation in the direction of arrow 136 until properly aligned. Therefore, such alignment advantage is beneficial, even if the ring becomes jostled from precise alignment prior to its application to the user's penis. Of course, the degree of advantage may vary depending on the design of the elastic ring utilized.

The following discussion more particularly relates to interference fit means and interference release means in accordance with the subject invention, and references more particularly illustrations of present FIGS. 7 through 10.

Figure 9:
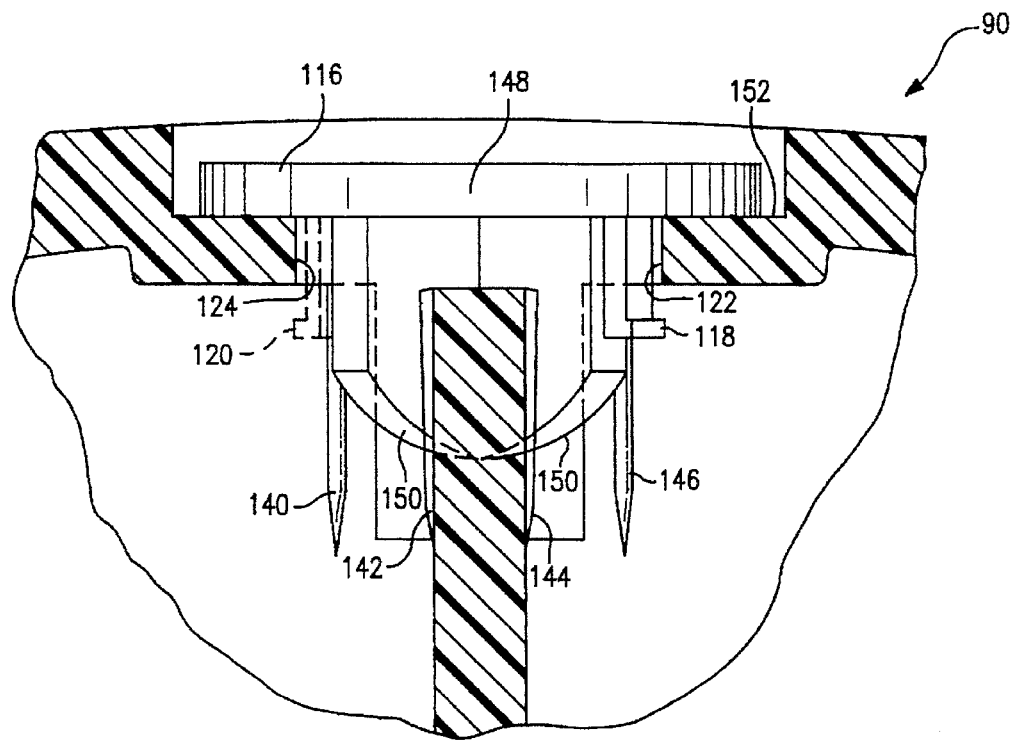
FIG. 9 is an enlarged, partial cross-sectional view of the subject matter of present FIG. 7, illustrating the position of the dome release button features while the expansion function is mid-way taking place.

In each of such Figures, dome 90 is shown in partial cutaway and/or partial cross-sectional view. FIG. 9 corresponds substantially with an enlarged illustration of the cutaway portion of FIG. 7, and FIG. 10 substantially is an enlargement of the cutaway portion of FIG. 8. FIGS. 5A and 5B also illustrate pertinent features of removable button or interference release means 116.

As best represented in FIGS. 7 and 9, the interior portion 134 of dome 9 includes at least one interference fit nodule 140, and preferably a total of four such nodules, further including nodules 142, 144, and 146. Removable button 116 has an upper cap 148 which is attached to its own four ribs or "X" key members 150. Such smaller key ribs 150 have rounded lower edges, similar to the extended portion 112 of dome 90. Dome 90 has a recessed area 152 for receipt of button 116, the depth of which space 152 may be varied so as to vary the range of motion of button 116. Members 118 and 120 are received through openings 122 and 124 (see also FIG. 5B) for selectively securing the removable button. To remove the button 116, elements 118 and 120 may be simply pressed radially inward to permit button 116 to be withdrawn. The axial length of members 118 and 120 also defines the range of motion for button 116, and such length may be varied as desired.

Figure 10:
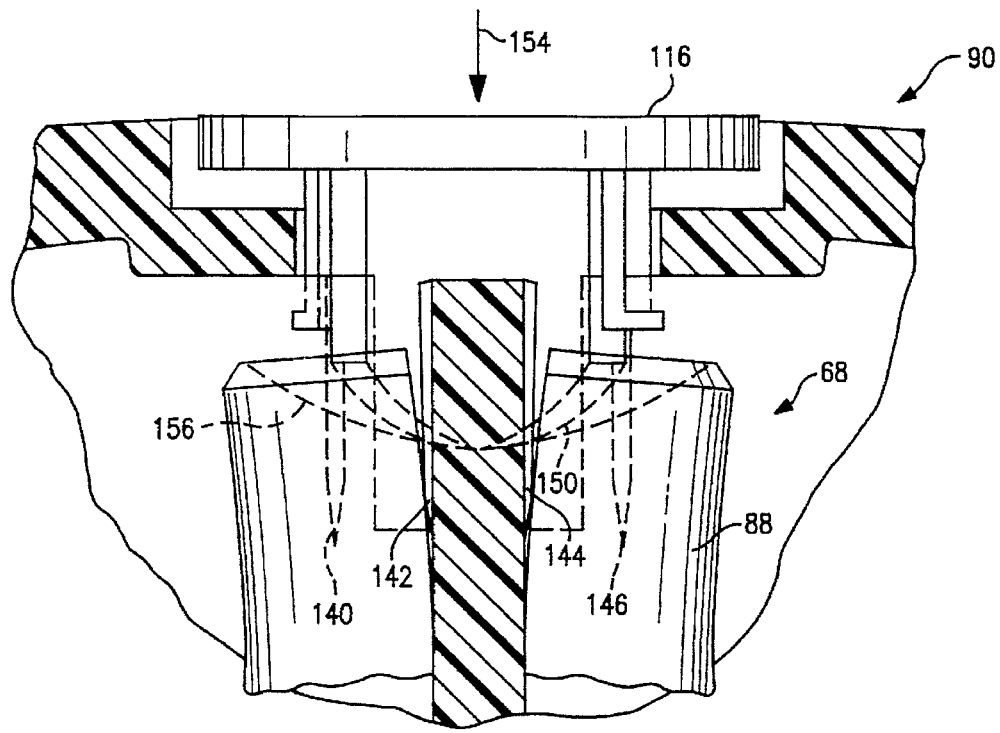
FIG. 10 is a cross-sectional view similar to that of FIG. 9, illustrating the cone and dome fully mated and the resulting position of the release button feature during interference fit of the tapered smaller end of the cone into the upper portion of the dome interior.

In the indicated configuration, particularly as represented by FIGS. 8 and 10, tapered smaller end 68 engages the interference fit nodules so as to be flexed thereby. The degree of flexure is exaggerated in FIGS. 8 and 10 for purposes of illustration. The flexure primarily may comprise radially outward expansion of the four sectors or regions formed in such end 68 due to the "X" keyhole arrangement therein, due to the slots or grooves, as discussed above.

As represented in FIG. 10, button 116 is thrust upwardly to accommodate the occurrence of such interference fit. It should be noted that the resulting interference fit is relatively only slight, but that is adequate for most purposes of simply holding the two components 58 and 90 together for their collective removal from a vacuum chamber or transfer collar, or other receiving element. Whenever desired, button 116 may be depressed in the direction of the cone component, i.e., in the direction of arrow 154. In the represented embodiment, the lower leading edge of elements 150 in turn engage surfaces, such as curved area 156, of the cone component, so as to drive it or separate it from the slight detent nodules, thereby releasing the slight interference fit.

It will be understood by those of ordinary skill in the art that other arrangements, such as including a reversal of parts or functions, may be practiced. For example, elements such as "bumps" or nodes may be placed on the cone member itself, and engaged with other internal features so provided on the dome interior. Nodes directly slightly inward of the keyhole region may engage a central post or element of the dome interior. Such an arrangement may be particularly useful in conjunction with increasing the degree of interference fit.

In any such embodiment with a relatively increased degree of interference fit, it may be desirable to lengthen the range of operation of button 116, as discussed above, so as to increase the release force obtained thereby, or to make other adjutments. For example, the number of griper elements 118 and 120 may be changed from 2 to some other number such as 8, with a corresponding increase in an engaging lip or similar feature. Also, the underside of button 116 may omit ribs 150 and instead directly engage an upwardly thrust portion of cone 58 or some other intermediate element provided. All such variations are intended to come within the spirit and scope of the present invention, by virtue of present reference thereto.

Figure 12:
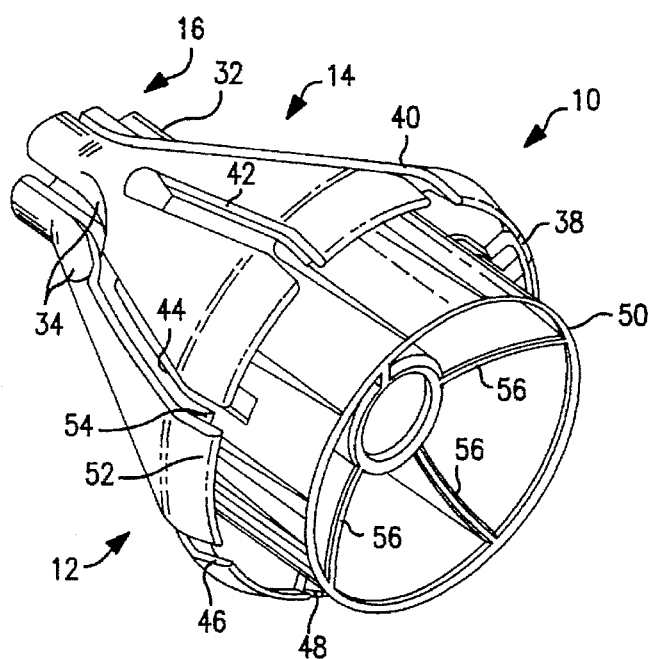
FIGS. 12 and 13 are respective cone and dome eight slot and eight rib matable components, illustrated in generally side and bottom perspective views, constituting alternative embodiments to the exemplary four slot and four rib cone and dome features of present FIGS. 2 through 8.

Those of ordinary skill in the art will appreciate that still further variations may be practiced in accordance with the subject invention. For example, FIG. 12 represents a combination of an eight-slot cone 10 with a particular elastic ring 18. FIG. 12 represents such cone 10, without any particular elastic ring, representative of the fact that alternative elastic rings may be utilized, as discussed above.

Figure 13:
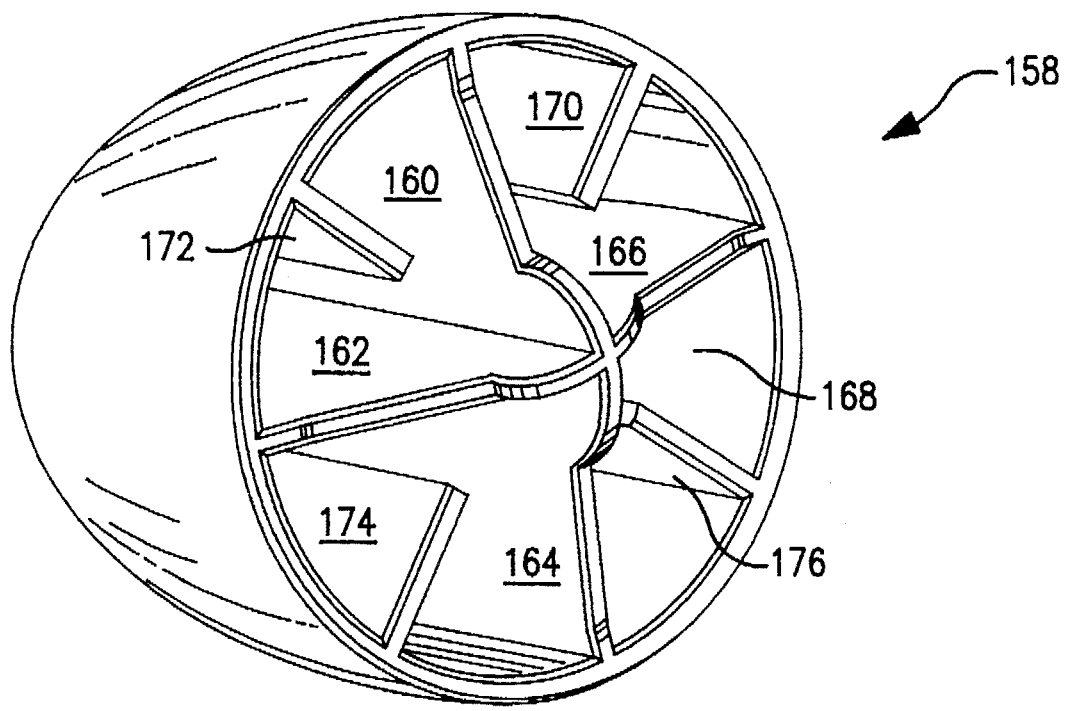

FIG. 12 is a generally side and bottom perspective view of such eight slot cone embodiment 10. Like reference characters of FIG. 1 represent corresponding features. FIG. 13 represents a further dome embodiment 158 which may be provided with eight ribs corresponding for use with the eight slots or grooves of the cone of FIG. 12.

The generally side and bottom perspective view of present FIG. 13, reveals four primary ribs 160, 162, 164, and 166 coming together to collectively form an "X" key region generally 168. Likewise, such area is generally extended, to facilitate initial alignment and engagement of dome 158 with cone 10. An additional four ribs 170, 172, 174, and 176 may be provided equidistant between the adjacent larger main ribs. Such additional ribs may in some embodiments further enhance stability of the mating travel of the dome down onto the cone. Such an arrangement may be particularly helpful where relatively higher strength rated tension rings are utilized, or where multiple rings (i.e., two or more elastic rings) are simultaneously expanded with the subject cincture band expansion means.

Still further, it will be understood by those of ordinary skill in the art that other embodiments, such as a two slot and rib cone and dome respective component ring loading device, may be provided in accordance with the subject invention, though not specifically illustrated herein. All such variations are intended to come within the spirit and scope of the subject invention, including odd numbers of such features, or including an embodiment without specific such alignment slots and ribs. Likewise, any equivalents thereof for performing an alignment function would be encompassed by such broader aspects of the invention.

Still further, various dimensional alternatives may be practiced, such that the present invention is not particularly limited to certain dimensions thereof. For the sake of example, the following are several exemplary dimensions which may be practiced in conjunction with cone 58 and dome 90.

The inside diameter of a vacuum chamber may typically be in a range of about 2 to 2.5 inches. Where such inside diameter is 2 inches, one preferred diameter of the reduced diameter base section 80 of cone 58 may be about 1.97 inches. The fully extended outside diameter 72 thereof, in such example, may be about 2.57 inches. The overall length between the two opposing ends of such example cone 58 may be about 3.2 inches, with the axial length of reduced diameter base section 80 being about 0.5 inches thereof.

The overall height of dome 90 may also be about 3.0 inches to about 3.35 inches. Other dimensions of both the cone and dome may follow accordingly, or be varied in accordance with different particular circumstances. Lightweight plastic materials may typically comprise suitable materials, with variations permitted.

As noted above, the subject invention equally pertains to corresponding methodologies for use of the subject ring loading device and/or combinations of such ring loading device or cincture band expansion means with particular cincture bands, vacuum chambers and/or transfer collars, as collectively comprising improved impotence treatment systems in accordance with the subject invention. It should be further understood by those of ordinary skill in the art that the foregoing presently preferred embodiments (both as to devices and methods) are exemplary only, and that the attendant description thereof is likewise by way of words of example rather than words of limitation, and their use does not preclude inclusion of such modifications, variations, and/or additions to the present invention as would be readily apparent to one of ordinary skill in the art, the scope of the present invention being set forth in the appended claims.

What is claimed is:

1. Improved impotence treatment system for augmenting male potency through vacuum-generated engorgement of the male sex organ and subsequent cincture thereof with a cincture band, said system comprising:

an elongated, generally cylindrical vacuum chamber adapted to cover a male sex organ, said vacuum chamber being open at a proximal longitudinal end thereof for contact with a user and for passage of the user's male sex organ therethrough into the interior of said chamber;

an elastic penile cincture band adapted to be expanded and located about said vacuum chamber proximal end for subsequent movement onto the base of a user's male sex organ for cincturing an engorged condition thereof; and cincture band expansion means removably associated with said vacuum chamber proximal end for expanding said cincture band and for locating same onto said vacuum chamber whenever said expansion means are associated therewith, said expansion means including expanding cone means for receiving thereon a cincture band to be expanded and including corresponding actuation means matable with said cone means for being pushed by a user down onto said cone means such that a cincture band received on said cone means is expanded for subsequent cincturing of a user's engorged male sex organ;

wherein said elastic penile cincture band has an inside diameter which is generally circular over the majority of such diameter, and which includes at least one noncircular inside diameter feature, and wherein said expanding cone means includes at least one surface contour element adapted for matable receipt of such cincture band noncircular inside diameter feature, for registration of said band.

2. A system as in claim 1, wherein said cincture band expansion means includes at least one cincture band registration element for predetermined rotational positioning of said elastic penile cincture band relative to said vacuum chamber.

3. A system as in claim 1, wherein said cone means includes a visual indicator element for indicating to a user the alignment on said cincture band noncircular inside diameter feature after enlargement of said cincture band against said cone means.

4. A system as in claim 1, wherein said cincture band inside diameter feature comprises a urethra channel, and wherein said expanding cone means matable surface contour comprises a generally longitudinally extending rib along the surface thereof adapted for mating with said urethra channel.

5. A system as in claim 4, wherein said cincture band further includes at least one radially inward point in said inside diameter thereof for providing added pressure at a selected penile site when applied to the male sex organ, and wherein said cone means includes a corresponding surface channel generally longitudinally therealong for mating with said radially inward point of said cincture band.

6. Improved impotence treatment system for augmenting male potency through vacuum-generated engorgement of the male sex organ and subsequent cincture thereof with a cincture band, said system comprising:

an elongated, generally cylindrical vacuum chamber adapted to cover a male sex organ, said vacuum chamber being open at a proximal longitudinal end thereof for contact with a user and for passage of the user's male sex organ therethrough into the interior of said chamber;

an elastic penile cincture band adapted to be expanded and located about said vacuum chamber proximal end for subsequent movement onto the base of a user's male sex organ for cincturing an engorged condition thereof; and cincture band expansion means removably associated with said vacuum chamber proximal end for expanding said cincture band and for locating same onto said vacuum chamber whenever said expansion means are associated therewith, said expansion means including expanding cone means for receiving thereon a cincture band to be expanded and including corresponding actuation means matable with said cone means for being pushed by a user down onto said cone means such that a cincture band received on said cone means is expanded for subsequent cincturing of a user's engorged male sex organ;

wherein said cincture band expansion means includes alignment means for aiding alignment and mating of said cone means and said actuation means.

7. A system as in claim 6, wherein said alignment means include at least one slot and corresponding matable ribbed element formed with said cone means and said actuation means, respectively, for alignment thereof.

8. A system as in claim 7, wherein:

said expanding cone means comprises a conical-shaped pyramid with four equidistant vertical grooves, having a cone slope in a range of about 15 degrees to about 45 degrees, and a reduced diameter base for extending downwardly into said vacuum chamber proximal longitudinal end; and said actuation means comprises a dome-shaped element including an inside matrix of four internal ribs, equally spaced for mating with said four cone means grooves, said ribs having angled leading edges in a range of about 15 degrees to about 45 degrees from a plane perpendicular to the direction of movement of said actuation means for being pushed by a user down onto said cone means, which angled leading edges engage said elastic penile cincture band received between said cone means and said actuation means, for expansion of said cincture band against said leading edges and against the outside surface of said cone means pyramid whenever said actuation means is pushed down onto said cone means.

9. A system as in claim 7, wherein there are a predetermined number of slots falling in a range of from two to eight slots, and wherein there are a matching number of ribbed elements.

10. A system as in claim 9, wherein there are four slots and four matable ribbed elements.

11. A system as in claim 9, wherein there are eight slots and eight matable ribbed elements.

12. Improved impotence treatment system for augmenting male potency through vacuum-generated engorgement of the male sex organ and subsequent cincture thereof with a cincture band, said system comprising:

an elongated, generally cylindrical vacuum chamber adapted to cover a male sex organ, said vacuum chamber being open at a proximal longitudinal end thereof for contact with a user and for passage of the user's male sex organ therethrough into the interior of said chamber;

an elastic penile cincture band adapted to be expanded and located about said vacuum chamber proximal end for subsequent movement onto the base of a user's male sex organ for cincturing an engorged condition thereof; and cincture band expansion means removably associated with said vacuum chamber proximal end for expanding said cincture band and for locating same onto said vacuum chamber whenever said expansion means are associated therewith, said expansion means including expanding cone means for receiving thereon a cincture band to be expanded and including corresponding actuation means matable with said cone means for being pushed by a user down onto said cone means such that a cincture band received on said cone means is expanded for subsequent cincturing of a user's engorged male sex organ;

wherein said cincture band expansion means further includes interference fit means for temporarily holding said expanding cone means and actuation means in mated relationship whenever said actuation means is pushed down onto said cone means by a user.

13. A system as in claim 12, wherein said cincture band expansion means further includes interference release means for permitting a user to selectively release an interference fit between said expanding cone means and said actuation means.

14. A system as in claim 13, wherein said interference release means comprises an actuation button removably received in a domed portion of said actuation means, for selective removal of such button to facilitate cleaning of the interior of said actuation means.

15. An improved impotence treatment method for augmenting male potency through vacuum-generated engorgement of the male sex organ and subsequent cincture thereof with a cincture band, usable with a system such as comprising an elongated, generally cylindrical vacuum chamber adapted to cover a male sex organ, which vacuum chamber is open at a proximal longitudinal end thereof for contact with a user and for passage of the user's male sex organ therethrough into the interior of such chamber, and using an elastic penile cincture band adapted to be expanded and located about such vacuum chamber proximal end for subsequent movement onto the base of a user's male sex organ for cincturing an engorged condition thereof, said improved method including the steps of:

providing a cone component comprising a generally conical-shaped pyramid adapted to be removably associated with the vacuum chamber proximal end for expanding the cincture band and for locating such cincture band onto the vacuum chamber outside diameter whenever the cone component is associated therewith;

providing a dome component matable with said cone component and adapted to be pushed down by a user onto such cone component such that a cincture band received on the cone component is expanded thereby for subsequent cincturing of a user's engorged male sex organ;

placing the cincture band onto the relatively smaller end of the cone component; and placing the dome component down onto the cone component with the cincture band seated thereon, and pressing downward for expansion of the cincture band.

16. A method as in claim 15, further including the step of placing a base end of the cone component into the vacuum chamber proximal end prior to the step of expanding the cincture band by pressing the dome component down onto the cone component.

17. A method as in claim 15, further including the steps of:
providing a generally annular transfer collar adapted for mating with the cone component; and
placing a base end of the cone component into said transfer collar prior to expansion of the cincture band by pressing the dome component down onto the cone component, so that the cincture band is expanded and moved onto the transfer collar for subsequent use.

18. A method as in claim 15, further including the step of providing at least one pair of respective alignment slot and rib elements on the respective cone and dome components, to facilitate keying of such components prior to their complete mating, and to continue alignment thereof during the working stroke of pressing the dome component down onto the cone component.

19. A method as in claim 15, further including the step of applying lubrication to the outer conical-shaped surface of the cone component prior to application of the cincture band and dome component thereto, such that completion of the expansion stroke is facilitated through lubrication and results in a sweeping action wherein the expanded cincture band resides in a lubricated position on one of a vacuum chamber or transfer collar, for ease of relative rotational adjustment thereof in relation to such receiving element.

20. A method as in claim 15, wherein the cincture band includes at least one inside diameter feature such as one of a urethra channel for accommodating the user's urethra or a radially inward point for added pressure to selected penile locations during cincturing operations, and wherein said method further includes the step of forming corresponding outer surface contours in said cone component for matable alignment and receipt of the cincture band inside diameter features.

21. A method as in claim 20, further including inclusion of a visual alignment feature for indicating to the user the cincture band registration as achieved through mating expansion of the cincture band relative to the cone component surface contours.

22. A ring loading device for use with an elastic ring of the type for augmenting male potency by cincturing an engorged condition thereof, said device comprising:
an expansion cone having a generally circular, enlarged base and a tapered outside surface reducing to a relatively smaller diameter end adapted for receipt thereabout of an elastic ring which is to be enlarged; and
an actuation dome adapted to be received downwardly about the tapered smaller end of said expansion cone and forced therealong, engaging an elastic ring received thereon for expansion of such ring towards the base of said expansion cone;
wherein said expansion cone includes at least one vertical groove therealong and said actuation dome includes at least one rib adapted to be received in said vertical groove for alignment of said cone and dome for facilitating relative movement therebetween.

23. A ring loading device as in claim 22, wherein said expansion cone includes four equally spaced vertical grooves and said actuation dome includes four correspondingly positioned ribs for respective mating with said four grooves.

24. A ring loading device as in claim 23, wherein said grooves and said ribs respectively intersect to form an "X" key for guided mating thereof.

25. A ring loading device as in claim 24, wherein said ribs include an extended region in the vicinity of said "X" key, for facilitating initial engagement of said ribs with said corresponding grooves.

26. A ring loading device as in claim 23, wherein said expansion cone has an outer surface slope in a range of about 15 degrees to about 45 degrees, and wherein a bottom portion of said four ribs are angled relative to a plane perpendicular to the line of movement of said actuation dome, which angle is in a range of about 15 degrees to about 45 degrees, for engagement with an elastic ring received between said expansion cone and said actuation dome during mating thereof.

27. A ring loading device as in claim 22, wherein said expansion cone includes eight equally spaced vertical grooves and said actuation dome includes eight correspondingly positioned ribs for respective mating thereof with said eight grooves.

28. A ring loading device as in claim 22, wherein said expansion cone includes at least one outer surface contour thereof for matable receipt with a corresponding feature formed in the inside diameter of an elastic ring used therewith, so as to properly and identifiably align such ring prior to and during expansion thereof.

29. A ring loading device as in claim 28, wherein said surface contour includes an elongated projection along the expansion cone outer surface for matable contact with an elastic ring urethra channel.

30. A ring loading device as in claim 29, further including a visual guide element extending along said expansion cone to the base thereof, for indicating the position of an elastic ring urethra channel after expansion of said ring.

31. A ring loading device as in claim 29, further including a pair of concave surfaces formed as contours in the outer expansion surface of said expansion cone, for mating receipt thereof with a corresponding pair of radially inward pressure elements formed in the inside diameter of an elastic ring applied thereto for expansion.

32. A ring loading device as in claim 22, wherein said dome includes at least one interference fit nodule within the interior thereof, for engagement with the tapered smaller end of said expansion cone whenever said cone and dome are fully mated, for a temporary interference fit therebetween.

33. A ring loading device as in claim 32, wherein said actuation dome further includes a disconnect button through the exterior of said dome opposite said interference fit nodule thereof, for selectively separating the mated cone and dome subsequent to use thereof.

34. A ring loading device as in claim 33, wherein said disconnect button is removable to facilitate cleaning the interior of said actuation dome.

* * * * *